(12) United States Patent
Delaveau et al.

(10) Patent No.: US 8,999,362 B2
(45) Date of Patent: Apr. 7, 2015

(54) LONG-ACTING NANOENCAPSULATED COUMARIN ARTHROPOD REPELLENT FORMULATIONS AND METHODS OF USE THEREOF

(71) Applicants: Jean Delaveau, Saint Nicolas de Macherin (FR); Audrey Minost, Villeurbanne (FR); Hatem Fessi, Villeurbanne (FR); Marie-Alexandrine Bolzinger, Lyons (FR); Abdelhamid Elaissari, Saint Genis-Laval (FR)

(72) Inventors: Jean Delaveau, Saint Nicolas de Macherin (FR); Audrey Minost, Villeurbanne (FR); Hatem Fessi, Villeurbanne (FR); Marie-Alexandrine Bolzinger, Lyons (FR); Abdelhamid Elaissari, Saint Genis-Laval (FR)

(73) Assignee: Merial, Inc., Duluth, GA (US)

( * ) Notice: Subject to any disclaimer, the term of this patent is extended or adjusted under 35 U.S.C. 154(b) by 24 days.

(21) Appl. No.: 13/751,787

(22) Filed: Jan. 28, 2013

(65) Prior Publication Data
US 2014/0213643 A1 Jul. 31, 2014

Related U.S. Application Data

(60) Provisional application No. 61/590,395, filed on Jan. 25, 2012.

(51) Int. Cl.
*A01N 25/12* (2006.01)
*A01N 43/16* (2006.01)

(52) U.S. Cl.
CPC ............ *A01N 43/16* (2013.01); *Y10S 977/906* (2013.01); *Y10S 977/915* (2013.01)

(58) Field of Classification Search
None
See application file for complete search history.

(56) References Cited

U.S. PATENT DOCUMENTS

2009/0010977 A1 1/2009 Xin

FOREIGN PATENT DOCUMENTS

| CA | 2181700 | 11/1996 |
|---|---|---|
| EP | 1 845 186 A1 | 10/2007 |
| KR | 100 727 236 B1 | 6/2008 |
| WO | WO 2011/012935 A2 | 2/2011 |
| WO | WO 2013/003168 A1 | 1/2013 |

OTHER PUBLICATIONS

Asnawi S et al: "Formulation of geranium oil loaded solid lipid nanoparticles for mosquito repellent application", J. Chem. and Natural Resources Engineering, vol. 2, Apr. 18, 2008, pp. 90-99.

(Continued)

*Primary Examiner* — Carlos Azpuru
(74) *Attorney, Agent, or Firm* — Judy Jarecki-Black; Chad Kitchen; Merial, Inc.

(57) ABSTRACT

The present invention relates to novel nanoencapsulated compositions, methods for making such compositions, and methods of repelling insects and other arthropod pests away from animals, including humans. The present invention has particular, though not sole, application to repelling insects including flies and mosquitoes. The inventive compositions may be used to repel arthropods from animals, humans, plants, soil, or building structures. The formulations also prevent illness and disease caused by insect/pest-borne vectors, and provide safer, more effective alternatives to existing repellents.

12 Claims, 8 Drawing Sheets

(56) References Cited

OTHER PUBLICATIONS

Asnawi S et al: "Effect of Variable Solvents on Particle Size of Geranium Oil-Loaded Solid Lipid Nanoparticle (Ge-SLN) for Mosquito Repellent Applications", A1P Conference Proceedings, Jan. 1, 2009, pp. 6-10.

Puglia C et al: "Evaluation of percutaneous absorption of the repellent diethyltoluamide and the sunscreen Ethylhexyl p-methoxycinnamate-loaded solid lipid nanoparticles: an in-vitro study", J. Pharmacy & Pharmacology, vol. 61, No. 8, Aug. 1, 2009, pp. 1013-1019.

Size as a function of process and formulation parameter.

20%  10%

LONG-ACTING NANOENCAPSULATED COUMARIN ARTHROPOD REPELLENT FORMULATIONS AND METHODS OF USE THEREOF

INCORPORATION BY REFERENCE

This application claims priority to U.S. provisional patent application Ser. No. 61/590,395, filed on Jan. 25, 2012, the disclosure of which is incorporated herein by reference.

FIELD OF THE INVENTION

The present invention relates to novel nanoencapsulated compositions, methods for making such compositions, and methods of repelling insects and other arthropod pests away from animals, including humans. The present invention has particular, though not sole, application to repelling insects including flies and mosquitoes. The inventive compositions may be used to repel arthropods from animals, humans, plants, soil, or building structures. The invention relates particularly to a nanoprecipitation process for small- to industrial-scale fabrication of nanoparticle/active ingredient suspensions having long-acting/slow-release properties.

BACKGROUND

Mosquitoes are disease vectors for human beings and animals, carrying malaria, heartworm, dengue fever, encephalitis, yellow fever and West Nile virus, and causing greater than 1 million human deaths around the world, every year. Health concerns and discomfort related to insect bites and stings have led to widespread use of insecticides and repellent products. Commercially available insecticides commonly include toxic active ingredients which act against the target pests. However if used in relatively confined environments and delivered as aerosol sprays these products can become toxic to humans and treated animals. Various undesirable side effects may include immediate or delayed neurotoxic reactions and/or suffocation. The noxious odor alone can cause headaches or nausea in some individuals. These adverse side effects are exacerbated when such compositions come in contact with persons of increased sensitivity, or persons of small body mass such as children or babies.

Therefore efforts have been made to develop insecticidal compositions non-poisonous to humans and pets. These non-poisonous insecticidal compositions available heretofore have had limited efficacy. Furthermore, although insecticides, which kill the target pests, are usually the quickest forms of treatment, they kill not only the undesired insects, but beneficial insects as well. Insect repellents may offer a compromise that minimizes disease and discomfort in animals, without disrupting the natural balance of insect populations. Several existing repellents are presented in Table 1.

TABLE 1

Commonly used repellents

| Name | Molecule | Molecular mass | Formula |
|---|---|---|---|
| Diethyl-toluamide (DEET) | | 191.13 | $C_{12}H_{17}NO$ |
| Picaridine | | 229.17 | $C_{12}H_{23}NO_3$ |
| Benzyl benzoate | | 212.08 | $C_{14}H_{12}O_2$ |
| Coumarin | | 146.15 | $C_9H_6O_2$ |

However, when used at concentrations effective to repel arthropod pests, existing repellents may also have toxic or otherwise undesirable consequences. Accordingly, there is a need for new formulations capable of effectively repelling pests, including insects, from animals, plants and building structures, and having improved safety and efficacy profiles. The formulations should be long lasting and of lesser toxicity than traditional repellents.

One possible solution to the problem may be the use of polymer-based colloidal particles, which have been largely used as solid support or carrier in numerous biomedical applications: latex or hybrid particles for in vitro biomedical diagnosis, biodegradable nanocapsules for in vivo drugs delivery (i.e. therapy), and in cosmetics. Biodegradable particles are particularly useful for therapy because they can be targeted to particular organs, tissues, cells or intracellular compartments via surface functionalization. Moreover, the use of active ingredient AI-loaded nanoparticles allows for both low-dose, continuous drug release, and local targeting, which together significantly reduce the severity of side effects as compared to, for example, those associated with systemic administration of the same AI.

TABLE 2

Insect repellent formulations described in the literature,
AI: Active Ingredient; DEET: N,N-diethyl-m-toluamide

| Form | AI | % AI | Formulation process | Reference |
|---|---|---|---|---|
| Microparticles | DEET | 15% w/w | Interfacial precipitation | [1] |
| Microparticles | Limonella oil | 30% v/v | Coacervation | [2] |
| Gel emulsion | DEET | 10% w/w | Emulsification | [3] |
| Nanoemulsion | Citronella oil | 20% w/w | High pressure homogenizer | [4] |

TABLE 2-continued

Insect repellent formulations described in the literature,
AI: Active Ingredient; DEET: N,N-diethyl-m-toluamide

| Form | AI | % AI | Formulation process | Reference |
|---|---|---|---|---|
| Nanoemulsion | Essential oils | 25% w/w | High pressure homogenizer | [5] |
| Solid lipid based nanoparticles | DEET | 10% w/w | Emulsification | [6] [7] |

One way to produce AI-loaded nanoparticles is via a process called "nanoprecipitation". U.S. Pat. No. 5,049,322 [8] (to CNRS) discloses a " . . . process for the preparation of dispersible colloidal systems in the form of spherical particles of the vesicular type and of a size less than 500 nm (nanocapsules), the wall of which is constituted by a substance A having film-forming properties and the core by a liquid substance B capable of being encapsulated by the substance A, comprising: combining (1) a first liquid phase consisting essentially of a solution of the substances A and B in a solvent for the substances A and B or in a mixture of solvents for the substances A and B, and (2) a greater amount of a second liquid phase consisting essentially of a non-solvent or a mixture of non-solvents for the substances A and B and including one or more surfactants, the solvent or the mixture of solvents of the first phase being miscible in all proportions with the non-solvent or mixture of non-solvents of the second phase, comprising a core of said liquid substance B surrounded by a layer of said substance A."

Upon addition of the organic phase into the aqueous phase and slow mechanical stirring, the nanoparticles are formed instantaneously by the rapid diffusion of the solvent in the aqueous phase. The latter is then removed by evaporation under reduced pressure. Acetone, Ethanol or their mixture are widely used as organic phase. The formation mechanism of the nanoparticles by this technique is explained by transitory interfacial turbulence due to the diffusion of organic solvent in water phase. The conditions to obtain nanoparticles should include the mutual and the total miscibility between solvents of the two phases and the fact that the mixture of the two solvents must be a poor solvent of the chosen polymer. Nanoprecipitation uses small quantities of surface-active agents, is rapid, and can easily be performed at industrial scale. However, this method is not indicated for the encapsulation of AI with little to no water-solubility. Further, the chosen organic solvent should be miscible in all proportions with the water phase, and the miscibility should be rapid in order to lead to a rapid nucleation process. FIG. 1 presents an illustration of the nanoprecipitation process.

The polymer matrix forming the particles is able to encapsulate basic organic molecules (i.e. therapeutic agents), organic macromolecules (lipids, carbohydrates), biomacromolecules (nucleic acids, proteins and peptides), metals, contrast agents, oils, radiolabeled elements, and the like. The formulation recipe choice is driven by the targeted application and more specifically, the desired characteristics as regards drug release profile and physicochemical stability. Polymer based nanoparticles have been a focus of numerous studies since 1980 [9]. The technology of nanoparticles offers many advantages, such as the solubilization of lipophilic molecules, increased bioavailability, and the protection of AI against physical, chemical, and biological degradations during storage and use.

The nanoparticles intended for a dermal use offer several advantages, mainly in comparison with the emulsions and the liposomes. The AI-loaded nanoparticles are able to cross the surface layers of the stratum corneum and to diffuse in the basal layers of the skin to specifically release the AI. This penetration into the deeper layers widens the action space of the AI and it protects the AI against rapid elimination by simple friction. The solid matrix nature controls the AI release through the skin. The occlusive effect caused by the deposition of nanoparticles increases the tank effect of the cornea layer and increases percutaneous absorption [10]. For a cutaneous application, the nanoparticle nature and size will condition the routing of the AI until the target site (pilous follicles, stratum corneum, epidermis, etc.) improving the tissue tolerance. In addition, by modulating the properties of nanoparticle surface, the composition and the medium, the desired release model of the AI and its biodistribution can be controlled.

The major characteristic of nanoparticle suspension preparation is the size of the formulated objects. Nanoparticle size depends in particular on solvent nature, active molecule concentration, organic phase/aqueous phase ratio, polymer, surfactant nature and percentage. Particle physicochemical characteristics can be specifically modified by judicious selection of polymer and surfactant properties (e.g. surface charge, porosity, biodegradability, etc.). Nanometric size and narrow size distribution lead to long term colloidal stability. A charged surface increases particle stability, and electrostatic surface modifications (with partially oppositely charged compounds) can contain target-specific ligands for improving passive and active targeting. Finally, the choice of solvent must be such that modifications of the physical properties of nanoparticles may occur. For example, a highly water miscible solvent (e.g., Dimethyl formamide, DMF) tends to diffuse into water faster than a solvent with lower water miscibility (e.g., acetone, tetrahydrofuran). The replacement of acetone by tetrahydrofuran is known to yield a decrease in particle size [11]. Polymers can be acquired commercially or synthesized from selected monomers or modified from preformed polymer, which allows for fine-tuning of the physicochemical properties of the final nanoparticles [12]. The particle size typically shows a linear correlation with the polymer concentrations because the number of particles remains essentially unchanged at the fixed condition [13].

Several factors impact particle size and size distribution. In general, a highly hydrophobic polymer in a highly water miscible solvent will nucleate very quickly and have a relatively smaller particle size. Surfactant presence in the formulation is a size control parameter; the nature and percentage allow achievement of a given particle size with a narrow size distribution. Finally, stirring process during the pouring of one phase in the other does not change the mean particle size, but does have tendency to decrease the polydispersity of the particles.

Active molecule hydrophobicity effect on the size and encapsulation efficiency of Indomethacin (hydrophobic) and doxorubicin (hydrophilic) formulated by nanoprecipitation using polylactide polymer shell were compared [14]. As example, Indomethacin-loaded nanoparticles provide a particle size of 190 nm with 80% of entrapped active molecule, against 290 nm and 50% of entrapped active molecule for Doxorubicin.

A major disadvantage of commercial pest repellent formulations has been the short duration of efficacy. Nanoparticle formulations could provide a useful solution, and as the above-described technologies have not yet been applied to the problem of pest repellency, it is an object of the instant invention to provide nanoparticle/AI formulations with improved safety and efficacy profiles, as compared with existing arthropod repellent formulations.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

A first object of the invention is to provide novel nanoparticle/AI formulations with improved safety and efficacy profiles, as compared with existing arthropod repellent formulations. The formulations are active in repelling pests, including insects and acarids, that are a burden to animals including humans. In some embodiments, the formulations are effective repellents against mosquitoes, flies, ticks, and fleas. The formulations may be dispersible colloidal systems produced by a nanoprecipitation process. In an embodiment, a lipophilic AI is encapsulated in the form of spherical particles (matrix type) having a diameter less than 500 nm.

In an embodiment, the formulations are highly effective arthropod repellents.

A second object of the invention is to provide a method of producing novel nanoparticle/AI formulations, which may comprise the following steps:

(a) preparing a liquid phase comprising a solution of an active ingredient in a solvent or a mixture of solvents comprising one or more surfactant;

(b) preparing a second liquid phase comprising a non-solvent or the mixture of non solvents for a substance that is miscible with the solvent or the mixture of solvents for the AI;

(c) adding one of the liquid phases prepared in (a) to (b) or (b) to (a) with stirring to produce a colloidal suspension of nanoparticles; and (d) optionally removing all or part of the solvent or the mixture of solvents to produce a colloidal suspension of nanoparticles of a desired concentration.

The formulations may comprise spherical nanoparticles of matrix type and size less than 500 nm, and be produced according to the following procedure:

(a) preparing a liquid phase comprising a solution of AI+polymer in a solvent or a mixture of solvents to which one or more surfactants may be added;

(b) preparing a second liquid phase comprising a non-solvent or a mixture of non-solvents to which one or more surfactant may be added, wherein the non-solvent or the mixture of non-solvents should be miscible in all proportions with the solvent or mixture of solvents of the AI;

(c) adding the liquid phase prepared in (a) to that prepared in (b), or adding the liquid phase prepared in (b) to that prepared in (a), with moderate agitation to produce a colloidal suspension of nanoparticles;

(d) optionally removing all or part of the solvent or the mixture of solvents and of non-solvent or mixture of non-solvent to make a colloidal nanoparticle suspension of a desired concentration.

The invention further relates to protecting an animal (e.g. a mammal or bird) against pests by administering an effective repelling amount of the formulations of the invention. Animals which can be treated include but are not limited to chickens/avians, humans, cats, dogs, cattle, cows, deer, goats, horses, llamas, pigs, sheep and yaks. In one embodiment of the invention, the animals treated are canines, felines, or humans.

The inventive formulations are highly effective for the repulsion of pests. Accordingly, the present invention provides methods for repelling pests away from animals, including humans, comprising applying a repulsive effective amount of the nanoparticle formulations, to the animal or human, or its surroundings.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims, terms such as "comprises", "comprised", "comprising" and the like can have the meaning attributed to such terms in U.S. patent law; e.g., they can mean "includes", "included", "including", and the like; and that terms such as "consisting essentially of" and "consists essentially of" have the meaning ascribed to them by U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
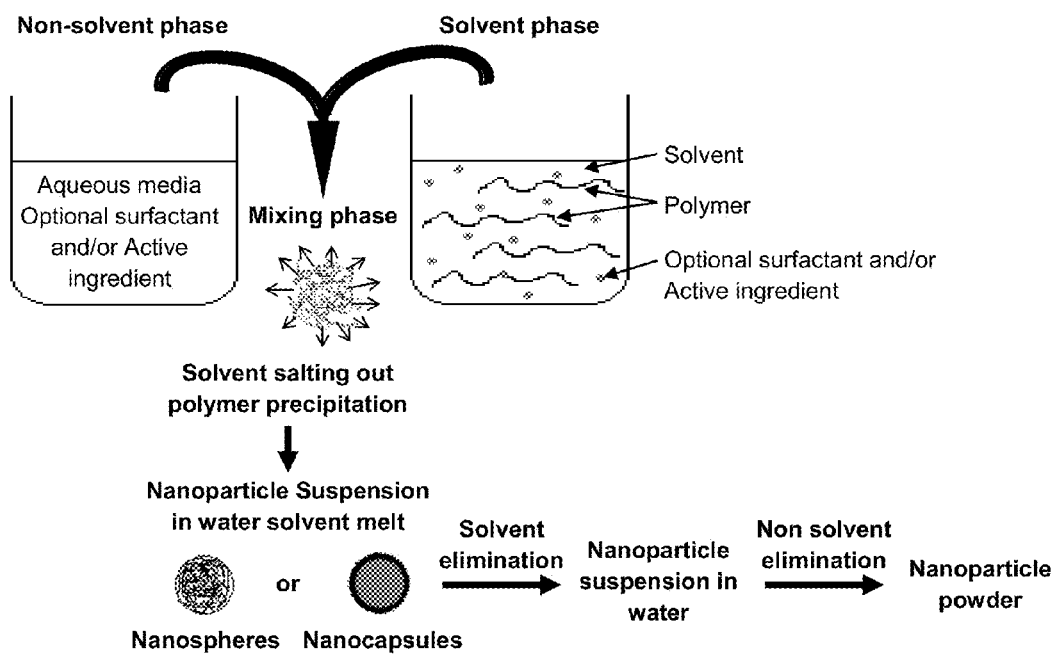
FIG. 1 depicts a nanoprecipitation process.
Figure 2:
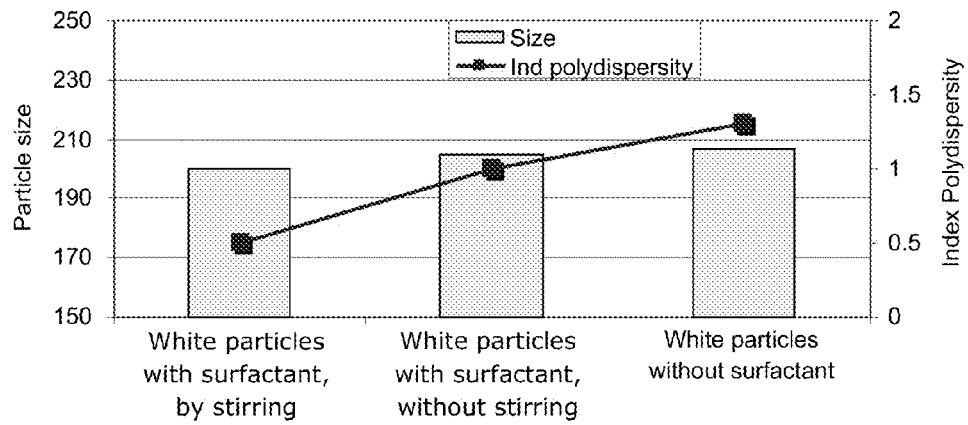
FIG. 2 is a graph indicating size and polydispersity index of polymer nanoparticles obtained by nanoprecipitation. Effect of surfactant and stirring process on size (Z-average, nm) and size distribution, determined by DLS (Dynamic Light Scattering) as analytical method.

The present invention provides novel nanoparticle formulations with insect and pest repellent activity, or pharmaceutically/veterinarily acceptable or pharmaceutically acceptable salts thereof, and compositions comprising the compounds or salts for the repulsion of insects or other pests away from an animal or a human. An important aspect of the invention is to provide nanoparticle formulations with high repellent activity against pests, particularly though not solely insects, and improved safety to the user, the environment, and the animal.

The invention includes at least the following features:

(a) In one embodiment, the invention provides novel nanoparticle formulations, which are repellents of animal pests, including insects and acarids;

(b) veterinary and pharmaceutical compositions for repelling pests comprising repellent effective amount of the nanoparticle formulations, in combination with a veterinarily or pharmaceutically acceptable carrier or diluent;

(c) veterinary and pharmaceutical compositions for repelling pests comprising a repellent effective amount of the formulations of the invention, in combination with one more other active agent, including other repellents, antiparasitics, and a veterinarily or pharmaceutically acceptable carrier or diluent;

(d) methods for producing the nanoparticle formulations;

(e) methods for repelling pests, including insects and acarids, away from an animal, including a human, are provided, which methods comprise administering a repellent effective amount of the nanoparticle formulations, to the animal in need thereof;

(f) methods for the prevention of infestation/infection and/or the reduction of transmission of a pest-borne pathogen to animals, including humans, which comprise administering a repellent effective amount of the nanoparticle formulations to the animal in need thereof, thereby preventing infection/infestation and/or reducing the transmission of pest-borne pathogens to animals, including humans;

(g) methods for controlling pests at a locus (e.g. by repelling pests away from a locus), comprising administering or applying a repellent effective amount of the nanoparticle formulations, to the locus; and (h) use of the nanoparticle formulations in the manufacture of a veterinary or pharmaceutical medicament for repelling pests, including insects and acarids.

A first aspect of the invention, therefore, is to provide novel nanoparticle/AI arthropod repellent formulations.

In an embodiment, the formulations may have improved safety and efficacy profiles, as compared with existing arthropod repellent formulations. The formulations may be active in repelling pests, including insects and acarids, that are a burden to animals including humans. In some embodiments, the formulations are effective repellents against mosquitoes, flies, ticks, and fleas.

In other embodiments, the formulations may be dispersible colloidal systems produced by a nanoprecipitation process. In an embodiment, a lipophilic AI is encapsulated in the form of spherical particles (matrix type) having a diameter less than 500 nm.

In an embodiment, the formulations are highly effective arthropod repellents.

A second aspect of the invention is to provide a method of producing novel nanoparticle/AI formulations, which may comprise the following steps:

(a) preparing a liquid phase comprising a solution of an active ingredient in a solvent or a mixture of solvents comprising one or more surfactant;

(b) preparing a second liquid phase comprising a non-solvent or the mixture of non solvents for a substance that is miscible with the solvent or the mixture of solvents for the AI;

(c) adding one of the liquid phases prepared in (a) to (b) or (b) to (a) with stirring to produce a colloidal suspension of nanoparticles; and (d) optionally removing all or part of the solvent or the mixture of solvents to produce a colloidal suspension of nanoparticles of a desired concentration.

The formulations may comprise spherical nanoparticles of matrix type and size less than 500 nm, and be produced according to the following procedure:

(a) preparing a liquid phase comprising a solution of AI+polymer in a solvent or a mixture of solvents to which one or more surfactants may be added;

(b) preparing a second liquid phase comprising a non-solvent or a mixture of non-solvents to which one or more surfactant may be added, wherein the non-solvent or the mixture of non-solvents should be miscible in all proportions with the solvent or mixture of solvents of the AI;

(c) adding the liquid phase prepared in (a) to that prepared in (b), or adding the liquid phase prepared in (b) to that prepared in (a), with moderate agitation to produce a colloidal suspension of nanoparticles;

(d) optionally removing all or part of the solvent or the mixture of solvents and of non-solvent or mixture of non-solvent to make a colloidal nanoparticle suspension of a desired concentration.

In an embodiment the nanoparticles may form instantaneously. The solution may become milky-white and show the typical "Tyndall effect" of colloidal suspensions. At this stage, it is preferable to add the liquid phase prepared in step (a) to the liquid phase prepared in the step (b), particularly if the latter is aqueous phase and more in the case of highly viscous phase prepared in the step (a), but the reverse order is possible as disclosed in examples (below). The encapsulated AI arthropod repellent prepared according to the process of the invention may be practically any substance sufficiently soluble in a given solvent or a melt thereof.

The particle matrix substance may be a synthetic, semi synthetic or natural polymer or a mixture thereof.

The invention particularly described the use of copolymer of acrylic acid (EUDRAGIT®).

The encapsulated substance may be an essential oil, a fatty substance alone or a dissolved AI, a pure AI or a crystal form thereof. The formulation can contain one AI or a mixture of AIs or an active ingredient dissolved in a specific medium. AIs include, but are not limited to pyrethroids (e.g. permethrin, cypermethrin, deltamethrin, cyphenothrin, etc.), acetamide derivatives (e.g. DEET, KBr3023, etc.), terpenoid derivatives (e.g. linalool, p-menthane 3-8-diol, geraniol, nepetalactone, etc.).

Now that the invention has been made, obvious variations will be readily apparent to skilled persons. For example, the process according to the invention can be applied equally well to one AI or to more than one AI. In an embodiment, a second AI may be bound by absorption to the surface of nanoparticles already formed in step (c) by simple addition to the colloidal suspension of the polymer.

In some embodiments, the solvent will be an organic solvent such that the liquid phase (a) will constitute an organic phase whereas the liquid phase (b) will constitute an aqueous phase. In other embodiments, it is possible to use either two organic phase or two aqueous phases provided the conditions regarding solubility and miscibility are met. In yet another embodiment, solvents must be sufficiently volatile to allow for removal thereof, if concentration of the nanoparticle formulation is desired or required.

In an embodiment, the solvent for the polymer may be chosen from among a lower alcohol (e.g. methanol, ethanol, isopropanol, etc.), a lower ketone (e.g. acetone, methyl ethyl ketone, etc.) a light hydrocarbon or a mixture of light hydrocarbons (e.g. hexane, petroleum ether, etc.), a chlorinated light hydrocarbon (e.g. chloroform, methylene chloride, trichloroethylene, etc.) or common light solvents such as acetonitrile, dioxane etc.

In an embodiment, the non-solvent or the mixture of non-solvents is a liquid which does not dissolve the substance while being miscible with the solvent used. Thus, when the substance is a polymer such as EUDRAGIT®, the solvent may be acetone or ethanol, and the non-solvent may be water.

In an embodiment, the surfactants of step (c) may be present in an amount from about 0% to about 10% (w/v).

In another embodiment, the concentration of the polymer in the solvent or the mixture of solvents may vary between about 0.1 and about 30%, and preferably between about 1% to about 15% by weight. The ratio of the solvents and non-solvents must be such as to allow the precipitation of the polymer. In an embodiment, increasing the solvent to non-solvent ratio decreases the size of the resultant nanoparticles.

In an embodiment where the amount of substances is sufficiently small, the moderate agitation of step (c) may be eliminated.

In another embodiment, the formulations may additionally comprise an electrolyte such as sodium chloride. In a particular embodiment, addition of up to about $10^{-2}$ M NaCl does not lead to coalescence or precipitation of the resultant nanoparticles.

In an embodiment nanoparticles smaller than 500 nm and having a narrow size distribution are produced using a method that does not require input of additional energy such as heat.

In another embodiment, polymers are selected from biocompatible polymers which may be naturally occurring polymers or synthetic polymers. Numerous innocuous polymers are well-known in the art and have long been and used for medical or cosmetic purposes.

In some embodiments, the solvent is biocompatible and need not be removed after formation of the nanoparticle formulations. In addition, the solvent may have preservative activity and/or be conducive to the production of formulations containing greater than about 20% of active ingredient, and/or conducive to the production of spherical nanoparticles exhibiting minimal size variation, for example, less than about 10% deviation from size average.

In other embodiment, the nanoparticles obtained are visible in the SEM and AFM, and appear to be approximately round in shape.

In an embodiment, the AI is selected from any disclosed in U.S. Ser. No. 61/501,485 or U.S. Ser. No. 61/538,425.

In one embodiment the AI may be a coumarin derivative of formula (I), or a veterinarily or pharmaceutically acceptable salt thereof:

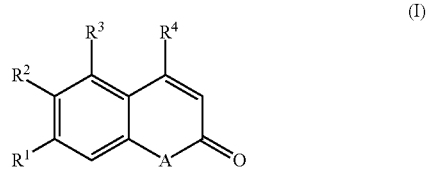

wherein
$R^1$, $R^2$, $R^3$, and $R^4$ independently include H, C, $OR^5$, $CR^5$, $OCC(=O)N(R^5)(R^7)$, $CC(=O)N(R^5)(R^7)$, alkyl, aryl, aralkyl, heteroaryl, alcohols, amine, aldehyde, heterocyclyl, or salts of amines and caboxylates; wherein A is O, or the ring is opened at A, thus forming compounds according to formula (Ia):

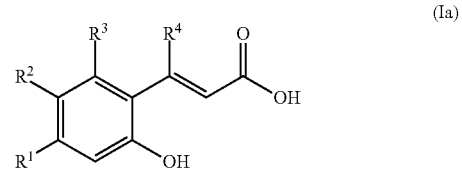

In another embodiment, the compound of formula (I) is EV04016, EV04024, EV04030, EV04032, EV04036, EV04054, EV04058, EV04062, EV04070, EV04084, EV04090, EV04094, EV04114, EV04122, EV04188, EV05056, EV05084, EV05088, EV05096, EV05118, EV05120, EV05134, EV05138, EV05144, EV05162, EV05174, EV05178, EV05184, EV06018, EV06020, EV06026, EV06028, EV06016, EV06044, EV06046, EV06048, EV06056, EV06058, EV06062, EV06068, EV06072, EV06086, EV06088, EV06092, EV06094, EV06096, EV06098, EV06110, EV06128, EV06136, EV06140, EV06144, EV06148, EV06154, EV06162, EV06166, EV06178, EV06188, EV07018.

In certain embodiments, the nanoparticle formulations of the invention are useful in veterinary applications, including for repelling pests, including insects and acarids, away from an animal. In other embodiments, the inventive nanoparticle formulations are useful in pharmaceutical or veterinary applications for repelling insects or acarids.

In another embodiment, the invention provides an insect/pest repellent composition comprising formulations of the instant disclosure.

In an embodiment, the composition is in a form suitable for topical application to an animal. The composition may be a cream, gel, spray, liquid or spot-on.

In an embodiment, the invention provides a method for repelling pests comprising the step of applying a nanoparticle formulation of any of the disclosed embodiments to animals or a locus.

In another embodiment the animals are birds or mammals.

In another embodiment the mammals are humans, equines, felines, canines, bovines, or caprines.

In another embodiment the animals are equines or bovines.

In another embodiment the animals are humans.

Other obvious variations on the above-recited embodiments will be appreciated by persons skilled in the art.

For convenience, certain terms employed in the Specification, Examples, and appended Claims are collected here.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

As used herein, the word "about", where it is specifically used to describe a concentration, a mass, a weight, or a volume, is hereby defined to mean "plus or minus 10%" of the stated value.

As used herein, the term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle), ovine (e.g., sheep), porcine (e.g., pigs), as well as avians. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary, and includes all avians kept as either companion or production animals.

As used herein, the term "aqueous suspension" includes mixtures of insoluble particles in water. Aqueous suspensions may contain the active material in admixture with excipients suitable for the manufacture of aqueous suspensions. Such excipients are suspending agents, for example, colloidal silica, sodium carboxymethylcellulose, methylcellulose, xanthan gum, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Veterinary Compositions:

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g. a stripe from head to tail of the animal.

Pour-on formulations are described in U.S. Pat. No. 6,010,710, also incorporated herein by reference. Pour-on formulations may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+$ $HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the formulation is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to about 10% weight/volume. In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

Methods of Treatment:

As discussed above, the nanoparticle formulations are effective in repelling insects and pests, and therefore may prevent insect/pest-borne infestations in animals or humans. In one embodiment, the invention provides a method for repelling insects or other pests away from an animal, comprising administering a repellent effective amount of a compound of formula (I) or (Ia), or veterinarily or pharmaceutically acceptable salts thereof, or a composition comprising the compounds, to the animal.

In still another embodiment of the invention, a method is provided for repulsion of insects/pests at a locus, which comprises administering or applying a repellent effective amount of a compound of formula (I) or (Ia), or veterinarily acceptable salts thereof, to the locus. With respect to animal health applications, "locus" is intended to mean a habitat, breeding ground, area, material or environment in which a parasite is growing or may grow, including in or on an animal.

Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Oxyuris* spp., *Toxocara, Strongyloides, Strongylus* spp., *Toxascaris, Trichinella, Trichuris,* and *Trichostrongylus*. The inventive compounds are particularly effective against organisms from the class of Protozoa, for example, *Eimeria* spp. and *Plasmodia* spp.

In each aspect of the invention, the compounds and compositions of the invention can be applied against a single organism/parasite or combinations thereof.

Additional pharmaceutical, pesticidal or veterinarily active ingredients, which include, but are not limited to, parasiticidals including acaricides, anthelmintics, endectocides and insecticides, may also be added to the formulations of the invention. Anti-parasitic agents may include both ectoparasiticidal and endoparasiticidal agents. Veterinary pharmaceutical agents are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrochysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, penicillins including penicillin G and penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds may be added to the compositions of the invention. Arylpyrazoles may include but are not limited to those described in U.S. Pat. Nos. 6,001,384; 6,010,710; 6,083,519; 6,096,329; 6,174,540; 6,685,954 and 6,998,131, all of which are hereby incorported by reference in their entirety, —each assigned to Merial, Ltd., Duluth, Ga.). A particularly preferred arylpyrazole compound that may be combined with the compounds of the invention is fipronil (5-amino-1-[2,6-dichloro-4-(trifluoromethyl)phenyl]-4-(trifluoromethylsulfinyl)pyrazole-3-carbonitrile, CAS No. 120068-37-3).

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962, 499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

The formulations of the invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and J.

Antibiotics 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In another embodiment, the formulations of the invention may be combined with cyclo-depsipeptide anthelmintic compounds including emodepside (see Willson et al., *Parasitology*, January 2003, 126(Pt 1):79-86).

In another embodiment of the invention, the class of acaricides or insecticides known as insect growth regulators (IGRs) may also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; U.S. Pat. No. 4,751,225, EP 0 179 022 or GB 2 140 010 as well as U.S. Pat. Nos. 6,096,329 and 6,685,954, all of which are hereby incorporated by reference in their entirety. Examples of IGRs suitable for use may include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that may be combined with the formulations of the invention may be a benzenedisulfonamide compound, which includes but is not limited to clorsulon; or a cestodal agent, which includes but is not limited to praziquantel, pyrantel or morantel.

In some embodiments, a parasiticidal agent that may be combined with the formulations of the invention may be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide may be emodepside.

In other embodiments, an insecticidal agent that may be combined with the formulations of the invention may be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are hereby incorporated by reference in their entirety.

For endoparasites, parasiticides which may be combined include but are not limited to pyrantel, morantel, the benzimidazoles (including albendazole, cambendazole, thiabendazole, fenbendazole, febantel, oxfendazole, oxibendazole, triclabendazole, mebendazole and netobimin), levamisole, closantel, rafoxanide, nitroxynil, disophenol and paraherquamide. For ectoparasites, insecticides which may be combined also include but are not limited to pyrethoids, organophosphates and neonicotinoids such as imidacloprid, as well as compounds such as metaflumizone, amitraz and ryanodine receptor antagonists.

The formulations of the invention may also comprise an antiparasitic macrocyclic lactone compound in combination with the active compound of the invention. The macrocyclic lactones include, but are not limited to, avermectins, such as abamectin, dimadectin, doramectin, emamectin, eprinomectin, ivermectin, latidectin, lepimectin, selamectin, ML-1,694, 554 and milbemycins, such as milbemectin, milbemycin D, moxidectin and nemadectin. Also included are the 5-oxo and 5-oxime derivatives of said avermectins and milbemycins. Examples of compositions comprising macrocyclic lactones include but are not limited to those described in U.S. Pat. Nos. 6,426,333; 6,482,425; 6,962,713 and 6,998,131, all of which are incorporated by reference in their entirety; —each assigned to Merial, Ltd., Duluth, Ga.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569, each of which is incorporated herein by reference. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all of which are incorporated by reference in their entirety. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all of which are incorporated by reference in their entirety.

In yet another embodiment of the invention, adulticide insecticides and acaricides can also be added to the formulations of the invention. These include pyrethrins (which include cinerin I, cinerin II, jasmolin I, jasmolin II, pyrethrin I, pyrethrin II and mixtures thereof) and pyrethroids, organophosphate (which included but are not limited to chlorfenvinphos, crotoxyphos, dichlorvos, heptenophos, mevinphos, monocrotophos, naled, TEPP, tetrachlorvinphos) and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In addition to the other active agents mentioned above, combinations of two or more active agents may be used with the formulations of the invention in a composition to treat a desired spectrum of pests and parasites. It would be well within the skill level of the practitioner to decide which individual compound(s) can be used in the inventive formulation to treat a particular infection of an insect.

REFERENCES

[1] Kasting G. B., Bhatt V., Speaker T. Microencapsulation decreases the skin absorption of N,N-diethyl-m-toluamide (DEET). Toxicology in Vitro 22 (2008) 548-552.
[2] Maji T. K., Baruah I., Dube S., Hussain M. R. Microencapsulation of Zanthoxylum limonella oil (ZLO) in glutaraldehyde crosslinked gelatin for mosquito repellent application. Bioresource Technology 98 (2007) 840-844.
[3] Qiu H., McCall J. W., Won Jun H. Formulation of topical insect repellent N,N-diethyl-m-toluamide (DEET): vehicle effects on DEET in vitro skin permeation. International Journal of Pharmaceutics 163 (1998) 167-176.
[4] Sakulku U., Nuchuchua O., Uawongyart N., Puttipipatkhachorn S., Soottitantawat A., Ruktanonchai U. Characterization and mosquito repellent activity of citronella oil nanoemulsion. International Journal of Pharmaceutics 372 (2009) 105-111
[5] Nuchuchua O., Sakulku U., Uawongyart N., Puttipipatkhachorn S., Soottitantawat A., Ruktanonchai U. In Vitro characterization and mosquito (Aedes aegypti) repellent activity of essential-oils-loaded nanoemulsions. AAPS PharmSciTech 10 (2009) 1234-1242.
[6] Iscan Y., Wissing S. A., Hekimoglu S., Müller R. H. Solid lipid nanoparticles (SLN) for topical drug delivery: incorporation of the lipophilic drugs N,N-diethylm-toluamide and vitamin. Die Pharmazie 60 (2005) 905-909.
[7] Yaziksiz-Iscan Y., Wissing S. A., Müller R. H., Hekimoglu S. Different production methods for solid lipid nanoparticles (SLN) containing the insect repellent DEET. Fourth World Meeting APGI/APV, Florenz, submitted for publication.
[8] Devissaguet, J P., Fessi, H., Puisieux, F. Process for the preparation of dispersible colloidal systems of a substance in the form of nanocapsules. U.S. Pat. No. 5,049,322 (1991).
[9] Schowalter, T D. 2006. Insect ecology. Academic Press.
[10] Dingler A., Runge S., et Müller R. H. SLN (Solid Lipid Nanoparticles) as drug carrier for an IV administration of poorly water soluble drugs. European Journal of Pharmaceutical Sciences 4 (1996) 132-132.
[11] Cheng, J., Tong, R. Particulate drug delivery. U.S. Pat. No. 0,248,126 (2008).
[12] Eliasof, S., Crawford, T. C., Gandal, G G., Relter, L A., Ng, P S. Polymer-agent conjugates, particles, compositions, and related methods of use. U.S. Pat. No. 0,247,669 (2010).
[13] Fisher, K., General, S. Functionalized, solid polymer nanoparticles comprising epothilones. U.S. Pat. No. 0,148, 384 A1 (2009).
[14] Stainmesse, S., Fessi, H., Devissaguet, J P., Puisieux, F., Thies, C. Process for the preparation of dispersible colloidal systems of a substance in the form of nanoparticles. U.S. Pat. No. 5,133,908 (1992).

The invention will now be further described by way of the following non-limiting examples.

EXAMPLES

The following examples are provided to illustrate certain embodiments of the invention and are not to be construed in any way as limiting the scope of the invention. In summary, nanoparticle suspensions were prepared, characterized in term of physicochemical parameters, drug release profile, repellent activity as long lasting efficiency were measured.

Briefly, the nanoparticle suspension preparation was the follow one: the arthropod repellent active ingredient, the polymer and the solvent were placed under magnetic stirring in order to obtain a perfectly homogeneous organic phase. This organic phase was poured under gentle magnetic stirring to the aqueous phase leading to the final nanoparticle suspension.

Example 1

Characterization of Arthropod Repellent-Loaded Nanoparticle Suspension

A reference formulation was produced, consisting of 10% (w/w) active ingredient (benzyl benzoate, BB); 10% (w/w) polymer (EUDRAGIT® S 100, "ERS100"); 30% (w/w) ethanol (EtOH) and 50% (w/w) deionized water. As defined herein, EUDRAGIT® S100 are anionic copolymers based on methacrylic acid and methyl methacrylate, and having CAS number 25086-15-1 and IUPAC name of "poly(methacrylic acid-co-methyl methacrylate) 1:2".

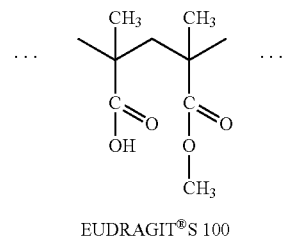

EUDRAGIT®S 100

The resulting formulation provided access to a stable, monodisperse nanosuspension with a Z-average of 150 nm and a Zeta potential of +50 mV. The difference in nanoparticle (NP) size, size distribution and Zeta potential between six NP batches of this reference formulation were statistically non-significant, reflecting the high reproducibility of the preparation method. The temperature range variation of both phases before nanoprecipitation was studied from 4 to 70° C. The size and Zeta potential analysis indicated the formulations obtained at different temperature (e.g. 4° C., 16° C., 20° C., 40° C., 50° C., 60° C., 70° C.) exhibited no significant differences as regards physicochemical characteristics. In agreement with the size and Zeta potential data, SEM showed the resulting NP possessed a highly similar surface aspect. The order of introduction (e.g. organic or aqueous phase first) had no significant effect on NP size, size distribution, Zeta potential and stability.

NP size/size distribution was measured on stable formulations. Overall, NP size averaged between 90 to 300 nm with monomodal population. The Zeta potential for all formulations was in the range of 50-60 mV, suggesting a net positive surface charge due to the functional group present on the polymer NP Loading Capacity with Varying BB/ERS100 Ratio.

Figure 3A:
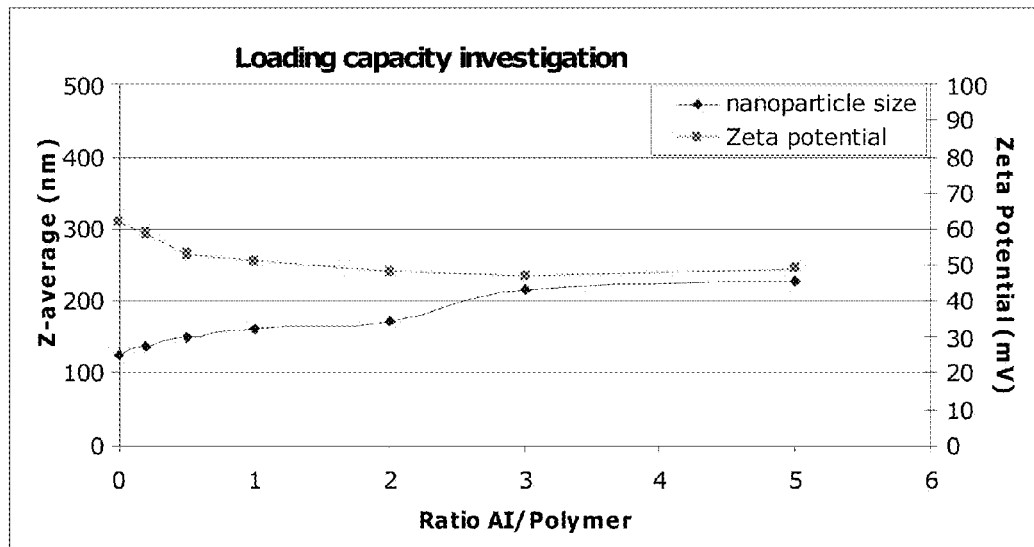
FIG. 3A is a graph depicting the evolution of the nanoparticle (NP) size (Z-average, nm) and zeta potential (mV) as a function of the ratio BB/ERS.
Figure 3B:
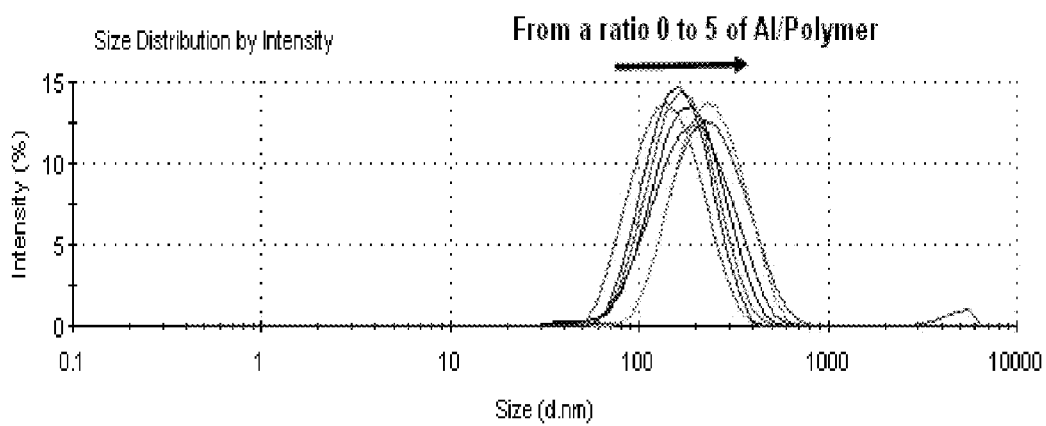
FIG. 3B is a graph depicting size distribution of the formulated NP suspension using DLS (dynamic light scattering) equipment.

The Z-average variation was determined to range from 110 to 210 nm (i.e. acceptable size range) over a broad BB:ERS100 range (from 11 to 0). AI loading capacity was evaluated, and as indicated by FIG. 3, NP size increased slightly with increasing AI content. The Zeta potential values decreased from 61 mV to 50 mV with increasing AI loading.

When the ratio of BB:ERS100 was fixed at 5, the corresponding formulation was stable, but presented a minor population of ~5 μm-sized NP, presumably due NP aggregation.

NP preparations with different ratio OP/AP were formulated; the percentages of recipes are gathered in Table 3:

TABLE 3

Formulation composition for (organic phase:aqueous phase) ratio study

|  | AM 0.14 | AM 0.35 | AM 0.7 | AM 1.4 | AM 2 |
|---|---|---|---|---|---|
| ERS100 (g) | 0.3 | 0.75 | 1.5 | 3 | 5 |
| BB (g) | 0.3 | 0.75 | 1.5 | 3 | 5 |
| EtOH (g) | 1.5 | 3.75 | 7.5 | 15 | 20 |
| Water (g) | 15 | 15 | 15 | 15 | 15 |
| Ratio OP/AP | 0.14 | 0.35 | 0.7 | 1.4 | 2 |

Figure 4:
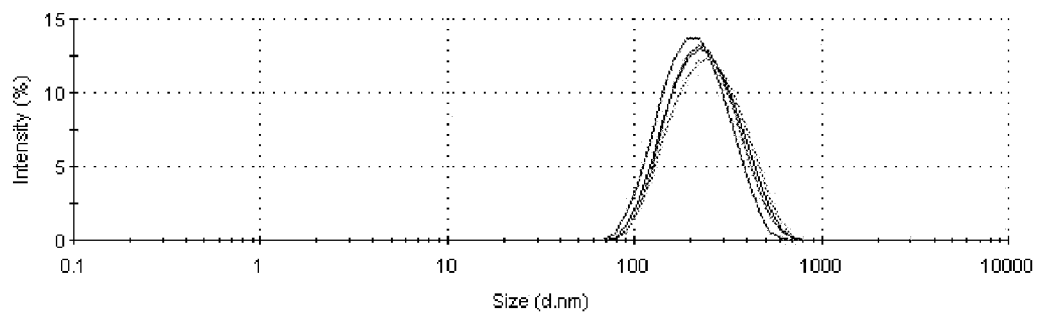
FIG. 4 is a graph depicting size distribution of the formulated NP produced during the organic phase (OP)/aqueous phase (AP) study.
Figure 5:
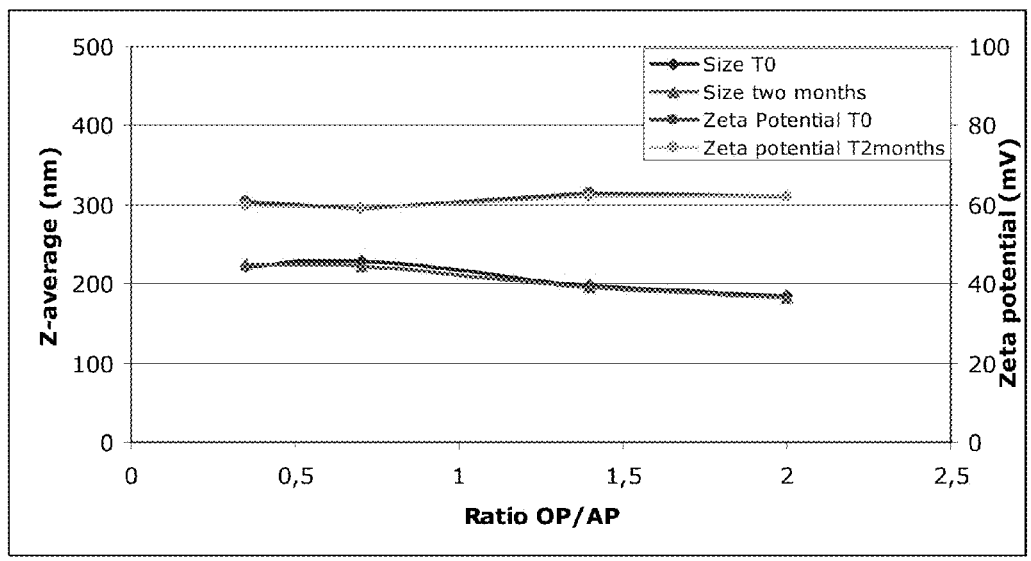
FIG. 5 is a graph depicting OP/AP ratio study for BB-loaded nanoparticle suspensions. Size (Z-average; nm) and Zeta potential (mV) were measured immediately following formulation and after 2 months at 40° C.
Figure 6A:
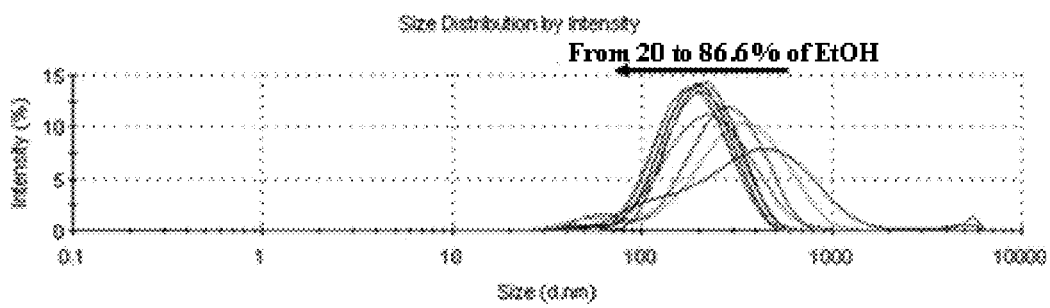
FIG. 6A is a graph of the DLA results for 9 formulations differing in EtOH percentage in the continuous phase.
Figure 6B:
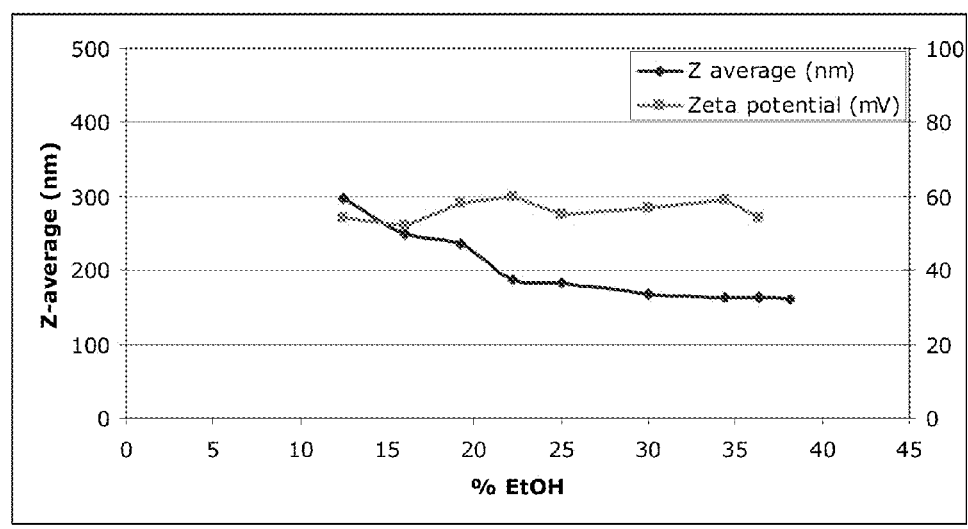
FIG. 6B is a graph depicting the NP size distribution for the 9 formulations.

Size analysis report obtained just after formulation presented a monodisperse NP size distribution, centered on 120 nm as shown in FIG. 4. These obtained analytical reports demonstrated no size changes for the formulations with a ratio OP/AP ranged from 0.14 to 1.4. Ratio OP/AP=5 was eliminated because it did not present stable, monomodal size distribution. The formulations were transferred to hermetic bottles in stored in an oven at 40° C., whereafter size and Zeta potential measurements/analyses were conducted at T=0, T=1 week, T=3 weeks, T=1 month and T=2 months. The results obtained for T0 and T2 months are presented in FIG. 5. Formulations of BB-loaded NP suspensions obtained by varying the OP/AP ratio did not present any instability phenomenon for a ratio ranged from 0.14 to 2. According to the size and size distribution study, formulations with a ratio ranged from 0.14 to 2 showed colloidal stability to at least 2 months at 40° C. The nearly identical Zeta potential value at T=0 and T=2 months provides further support the NP formulations are stabile for at least 2 months at 40° C.

Organic Solvent Content Study.

The solubility of BB in a mixture of ethanol and water was then evaluated (Table 3).

TABLE 1

Formulation and analytical data for the solvent content study; % EtOH is the solvent percentage in the continuous phase (EtOH + water).

|  | AM 6.6 | AM 13.3 | AM 20 | AM 26 | AM 33.3 | AM 40 | AM 46.6 | AM 60 | AM 73.3 | AM 80 | AM 86.6 |
|---|---|---|---|---|---|---|---|---|---|---|---|
| % EtOH | 6.6 | 13.3 | 20.0 | 26.7 | 33.3 | 40.0 | 46.6 | 60.0 | 73.3 | 80.0 | 86.6 |
| Size (nm) @ T0 | NA | NA | 298 | 249 | 236 | 187 | 182 | 167 | 163 | 162 | 160 |
| Zeta potential (mV) T0 | NA | NA | 56 | 54 | 52 | 58 | 60 | 55 | 57 | 59 | 54 |

Figure 7:
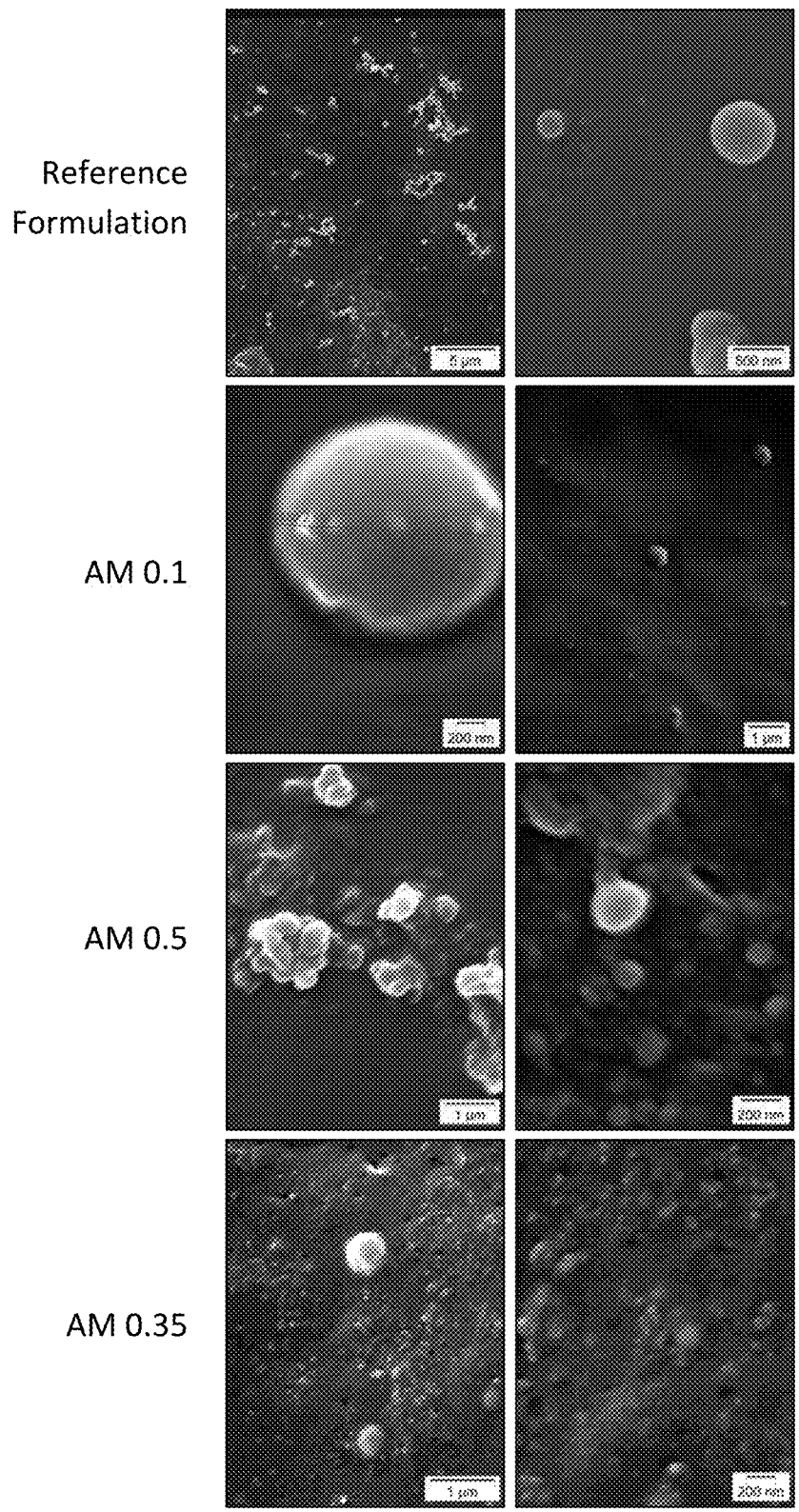
FIG. 7 are SEM micrographs of BB-loaded NP suspensions: AM 0.1 and AM0.5 were formulated with a ratio of OP:AP=0.1 and 0.5, respectively; AM 0.35 and AM 2 were formulated with a ratio of BB:ERS100=0.35 and 2, respectively

The formulations displayed monomodal distributions for EtOH content greater than 40% in the continuous phase, with particle diameters ranging from 187 nm to 160 nm, and polydispersity indices ranging from 0.080 to 0.150. The formulations also demonstrated excellent physical storage stability (40° C.) over long periods of at least 2 months. Comparison of NP size with the BB solubility indicated that increasing EtOH % results in greater amounts of BB in the continuous phase, with concomitant reduction in particle size. The data suggest that with 40% of EtOH in the continuous phase, approximately 2.4 mg/ml of BB will not be associated with NP. FIG. As indicated by SEM (FIG. 7), BB-loaded NP generated by nanoprecipitation were spherical with smooth surfaces and had diameters between 250 and 90 nm, in accordance with DLS data. As expected, the SEM measurement indicated slightly smaller NP sizes, relative to the DLS measurement, because DLS necessarily includes any solvation shell surrounding the NP. After complete drying, several BB-loaded NP appeared to have self-assembled into spherical aggregates.

pH Study.

Figure 8:
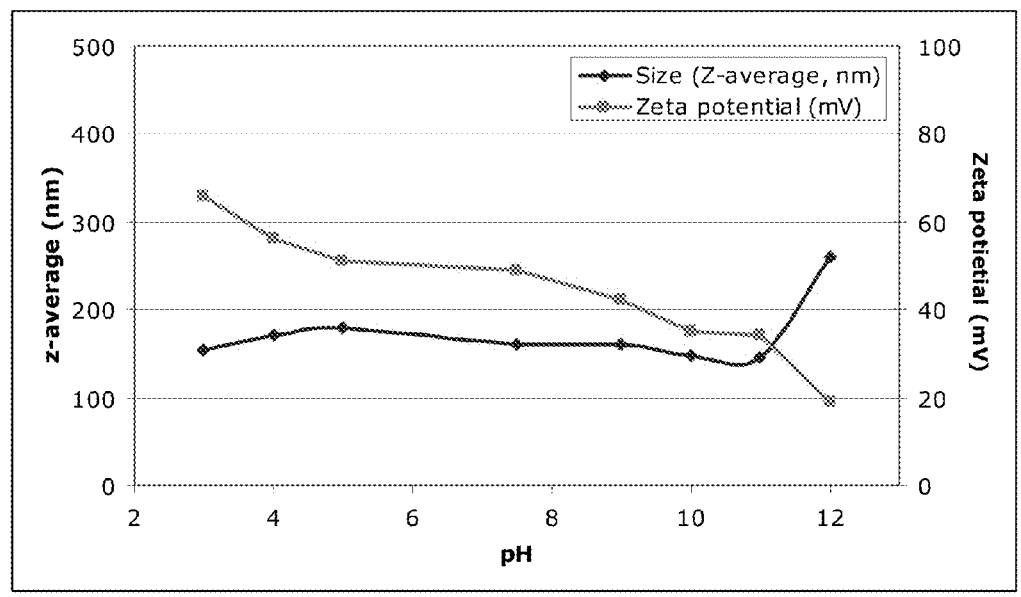
FIG. 8 is a size and zeta potential stability investigation of an optimized formula; shows the effect of pH on the colloidal stability of BB-loaded NP suspension

NP were formulated in an aqueous phase composed of deionized water and size, size distribution and Zeta potential were measured as before (FIG. 8). The diluted suspensions were composed to 0.5% (w/w) of loaded nanoparticles. Dispersion of the reference nanoparticle suspension in water at a pH range from 3 to 10 resulted in a stable NP suspension. The Zeta potential had a maximum value of +66 mV at pH=3, decreased with increasing pH, and reached a minimal value of +35 mV at pH=10. At pH greater than 10, the BB-loaded NP formulations showed heavy aggregation resulting in object which were too large to be measured by DLS.

Salinity Study.

Figure 9:
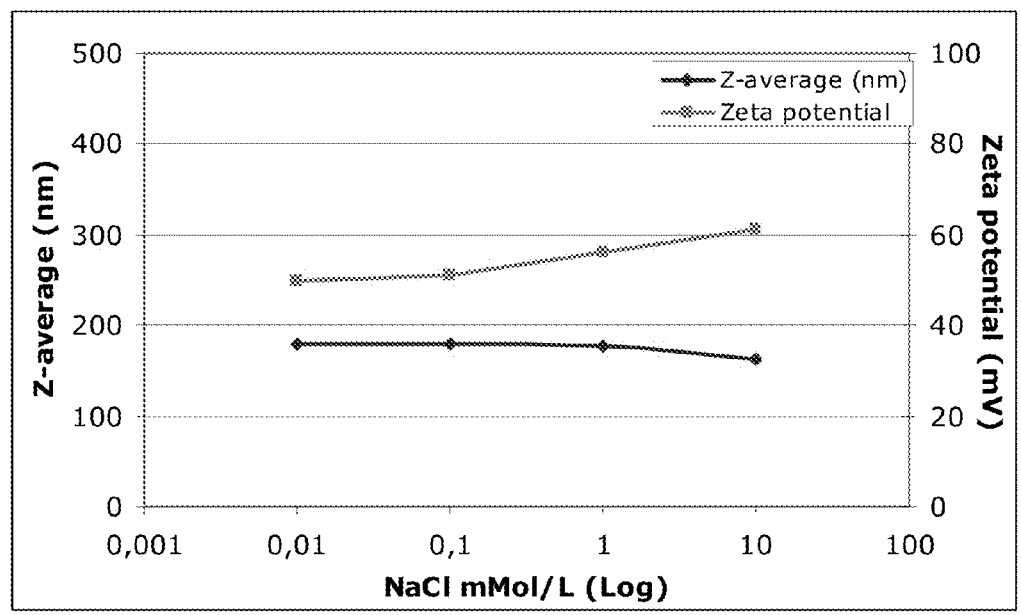
FIG. 9 is a graph depicting NP stability for formulations with varying salinity content in the continuous phase.

The stability of the samples was studied by analyzing the evolution of the particle diameters at different salt concentrations using sodium chloride. FIG. 9 displays the results for BB-loaded NP obtained from the reference formulation at pH 6.5 in the presence of NaCl. Briefly, a preselected volume of the reference BB-loaded NP formulation was diluted in a fixed aqueous volume at various salinity values. The bottles were sealed and suspension was stirred for 24 hours at room temperature. Particle size was analyzed by DLS after 24 hours of stirring. A low salt content did not appear to disrupt the NP stability in suspension. A NaCl content at 10 mMol/L slightly influenced the NP stability, as indicated by a Zeta potential increase.

Example 2

Repellent Nanoparticle Suspensions

Formulation I—AI-Loaded NP Using Non Ionic Surfactant.

ERS100, Benzyl Benzoate and acetone were stirred until the polymer was completely dissolved. The aqueous phase consisting of 0.1% (w/v) of Polysorbate 80 was prepared. The organic phase was poured into the aqueous phase with gentle stirring. Acetone was then removed and physicochemical characterization was performed. The obtained particles presented a size of 125 nm with a narrow distribution and a positive Zeta potential (+30 mV). These suspensions showed a colloidal stability for 4 weeks at 40° C.

Formulation II—AI-Loaded NP Using a Polymeric Surfactant.

Formulation II was prepared according to above procedure, though in this case, the organic phase was composed of polyvinyl alcohol 3-88 polymer, from 0.1 to 0.5% w/v in water. The obtained particles presented a size from 147 to 166 nm with a narrow distribution and a positive Zeta potential (+40 mV+/−5 mV). These suspensions showed a colloidal stability for 4 weeks at 40° C.

Formulation III—AI-Loaded NP Using Different Solvents.

Ethanol (III-a), Methanol (III-b), N,N-diethyl-acetamide (III-c) and isopropanol (III-d) were tested using the follow formulation and process: The organic phase was prepared dissolving the polymer and the AI. 2 g of ERS and 2 g of BB were dissolved in the solvent. The aqueous phase (deionized water) was placed under gentle magnetic stirring and the homogeneous organic phase was then added. The obtained NP with ethanol, methanol and isopropanol did not demonstrate significant difference in term of particle size, polydispersity or surface charge (150 nm; narrow size distribution; +60 mV+/−5 mV). With N,N-dimethyl-acetamide, the particle size was 370 nm with a narrow distribution. These NP suspensions exhibited colloidal stability for 4 weeks at 40° C.

Formulation IV—Essential Oil-Loaded NP.

Various essential oils were formulated by above-described nanoprecipitation process. 3 g of essential oils, 3 g of ERS and 9 g of EtOH were stirred until complete polymer dissolution. The aqueous phase consisted of deionized water was placed under stirring and the organic phase was then added, resulting in the essential oil-loaded NP suspension. Table 4 presents several physical parameters of suspensions made from different AI.

TABLE 4

Essential oil NP characteristics.

| Formulation ID | Essential oil | Particle size (nm) | Polydispersity index |
|---|---|---|---|
| IV-a | Bergamot | 500 | 0.200 |
| IV-b | Lemongrass | 186 | 0.160 |
| IV-c | Tagetes | 230 | 0.180 |
| IV-d | Lime | 360 | 0.200 |
| IV-e | Lavender | 140 | 0.136 |
| IV-f | Citronella | 227 | 0.150 |
| IV-g | Peppermint | 182 | 0.160 |
| IV-h | Rosemary | 210 | 0.180 |
| IV-i | Geranium | 178 | 0.140 |

Formulation V—AI-Loaded NP Using Polycaprolactone Polymer (PCL).

Polycaprolactone (0.5 g), ERS100 (2.5 g), BB (3 g), EtOH (9 g), and acetone (4 g) were placed under stirring until complete dissolution of the polymers. Thirty milliliters of deionized water was then placed under gentle stirring, and the organic phase was introduced thereto. Formulations presented a narrow size distribution centered on 150 nm.

Formulation VI—"Melt" AI-Loaded NP.

Either a melt of DEET and BB (VI-a), or a melt of picaridine and DEET (VI-b) were combined with ERS 100, EtOH, and water to produce NP suspensions using described methods. In both cases, the resulting NP suspensions presented a narrow size distribution centered on 200 nm+/−40 nm.

Formulation VII—of a New Molecule Having an Arthropod Repellent Power, a Coumarin Derivative.

A newly synthesized coumarin derivative, EV6062 (please see U.S. 61/501,485, to Merial, which is herein incorporated by reference in its entirety) was formulated by the nanoprecipitation process described for Formulation II.

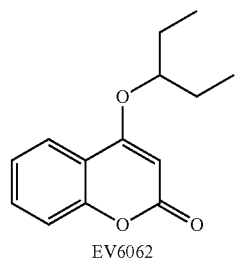 [SMILES: CCC(CC)Oc1cc(=O)oc2ccccc12]

EV6062

Briefly, EV6062 AI in the form of crystal was dissolved in EtOH with EUDRAGIT® S100 (ERS100) polymer to form a completely homogeneous organic phase. The organic phase was poured into the aqueous phase (deionized water), and mixed with stirring at room temperature. Immediately following formulation, the NP suspension presented a narrow size distribution centered on 175 nm. After 1 month at 25° C., no change was observed, indicating the formulation has desirable storage stability.

Example 2

In Vivo Bioassays on *drosophila* vs. Drug Release Profile

Figure 10:
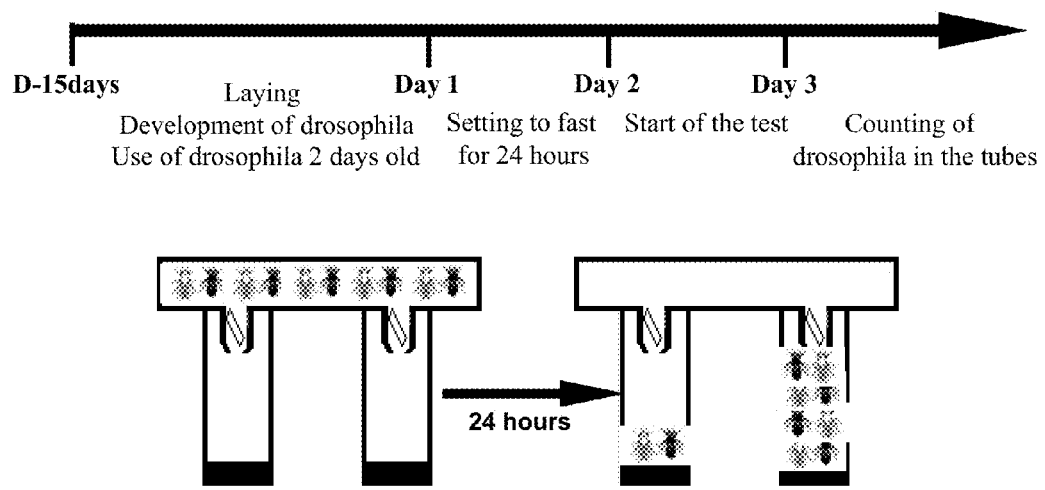
FIG. 10 depicts the experimental design.
Figure 11:
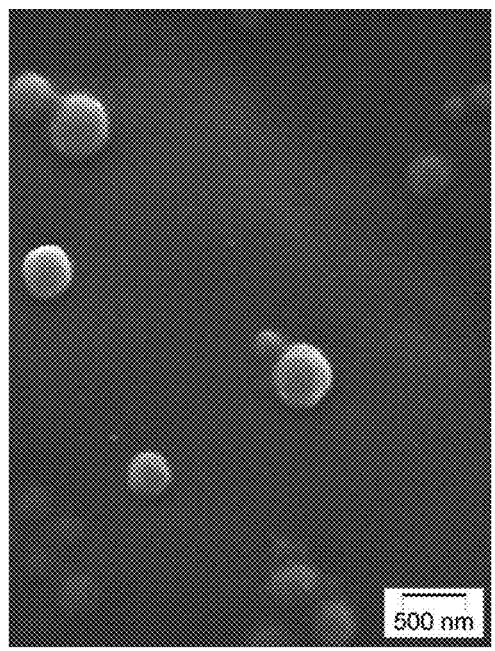
FIG. 11 presents an electron micrograph and a graphical plot of the NP for a BB-loaded NP suspension.
Figure 11:
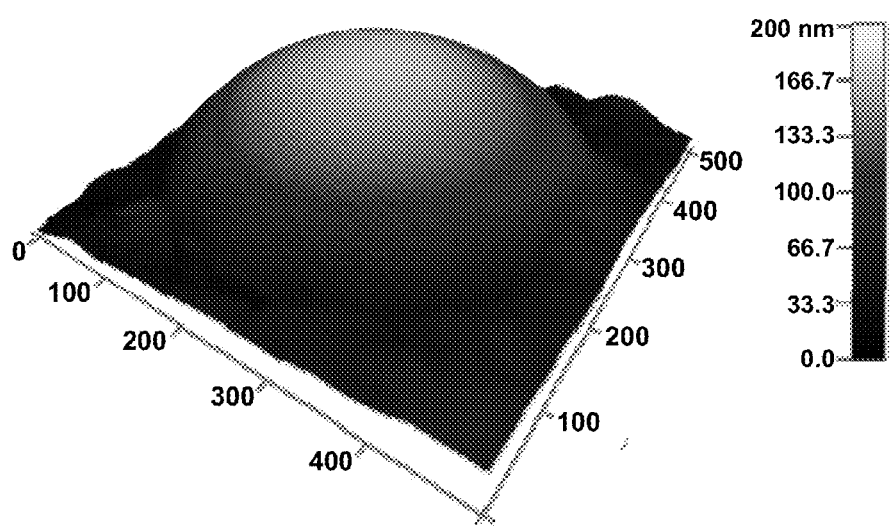

To investigate the effect of insect repellent formulations on food seeking behavior of *Drosophila melanogaster*, traps were baited with attractive food. FIG. 10 provides the experimental schema. The boxes were drilled to produce holes for the introduction of 1 ml eppendorf tubes, which were used as funnels between the higher box and the feeding tubes. The cap of each tube was removed and an opening of predetermined size was cut. Appropriate sized filter paper (10 mm×15 mm) was placed inside the tubes. Nutrient media principally was composed of corn flour, agar and yeast as attractant media and neatly disposed at the bottom of tubes.

In a temperature controlled room with a control *Drosophila melanogaster* two days old were fasted for 24 hours. Thirty minutes before the introduction of *drosophila*, 10 μl of tested product and formulation without AI were introduced using a 10 μL-micropipette. *Drosophila* were introduced, the box was closed and the experiment was carried out for 24 hours. After the experimentation time, mortality was counted in the top box and in tubes. *Drosophila* were immobilized with carbon dioxide gas and then counted. Ten experimental boxes were used Khi2 calculation was processed in order to validate the statistic result. A repellency power index and the standard error of the mean were calculated according to the follow equations:

$$(N1-N2)/(N1+N2)=RI$$

With N1 the number of non repelled *drosophila* and N2 the number of repelled *drosophila*. Index of repellence (RI) translates the repellent power of the formulation, comprised between 0 and 1. All the positive values translated repellent power. All tests were carried out on at least 6 experimental devices. For the drug release profile determination, filter papers in 0.5 ml-eppendorf tubes, the same experimental device used in the bioassays, were employed for the drug release profile performed. Filter papers, dimensions 1.5×0.5 cm, were introduced in 0.5 ml eppendorf tubes cap less truncated at the extremity. Tested formulations were introduced on the filter paper by weighting (10 mg+/−2 mg). Eppendorf tubes containing filter papers were placed on a polystyrene support and introduced in an oven at 32° C. with a slight air circulation. All experimental points were made in quadruple.

For the BB-loaded NP suspension vs. BB solution, differences in term of drug release profile and in term of Repellent Index were demonstrated (Table 5).

TABLE 5

| BB-loaded NP | | | |
|---|---|---|---|
| | Dose μg/cm$^2$ | Repellent index | Duration |
| Nanoparticles | 600 | 0.6 | immediately |
| | 400 | 0.5 | 24 hours |
| | 250 | 0.2 | 120 hours |
| Solution | 600 | 0.75 | immediately |
| | 450 | 0.5 | 6 hours |
| | 300 | 0.2 | 12 hours |

For the Picaridine, three formulations were tested and compared to the solution of active ingredient. Picaridine nanoparticles were on three forms, which vary for their ratio active ingredient over polymer (Table 6).

TABLE 6

| Picaridine-loaded NP. | | |
|---|---|---|
| | Repellent index | Duration |
| Nanoparticles A ratio 1:1 | 0.9 | Immediately |
| | 0.8 | 24 hours |
| | 0.6 | 72 hours |
| Nanoparticles A ratio 1:2 | 0.6 | Immediately |
| | 0.7 | 24 hours |
| | 0.75 | 72 hours |
| Nanoparticles A ratio 2:1 | 0.9 | Immediately |
| | 0.65 | 24 hours |
| | 0.58 | 72 hours |
| Ethanol Solution | 0.9 | Immediately |
| | 0.5 | 24 hours |
| | <0.3 | 72 hours |

Beneficial influence of polymer-based nanoparticles was demonstrated by a prolonged activity against *drosophila melanogaster* as insect model.

Prophetic Example

Compounds are applied to animals and surroundings to repel pests.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An arthropod-repellent nanoparticle formulation comprising at least one active ingredient (AI) selected from one or more coumarin derivatives according to formula (I) or (Ia):

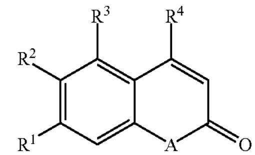

(I)

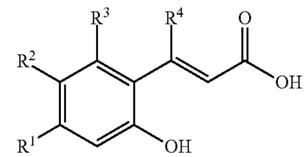

(Ia)

wherein $R^1$, $R^2$, $R^3$, $R^4$, and $R^6$ independently include H, C, $OR^5$, $CR^5$, $OCC(=O)N(R^5)(R^7)$, $CC(=O)N(R^5)(R^7)$, alkyl, aryl, aralkyl, heteroaryl, alcohols, amine, aldehyde, heterocyclyl, or salts of amines and caboxylates;

A is O, or the ring is opened at A, thus forming compounds according to formula (Ia);

$R^5$ and $R^7$ are independently selected from alkyl, aryl, aralkyl, heteroaryl, alcohols, amine, aldehyde, or heterocyclyl; or $R^5$ and $R^7$ come together to form a $C_3$-$C_{10}$ ring, which may be aromatic, non-aromatic, and/or substituted with alkyl, aryl, aralkyl, heteroaryl, alcohols, amine, aldehyde, heterocyclyl, or combinations thereof.

2. The formulation of claim 1 wherein the AI is EV6062

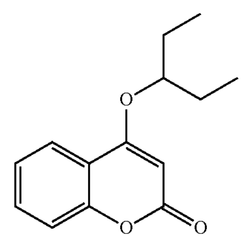

,

EV04016, EV04024, EV04030, EV04032, EV04036, EV04054, EV04058, EV04062, EV04070, EV04084, EV04090, EV04094, EV04114, EV04122, EV04188, EV05056, EV05084, EV05088, EV05096, EV05118, EV05120, EV05134, EV05138, EV0544, EV05162, EV05174, EV05178, EV05184, EV06018, EV06020, EV06026, EV06028, EV06026, EV06044, EV06046, EV06048, EV06056, EV06058, EV06062, EV06068, EV06072, EV06086, EV06088, EV06092, EV06094, EV06096, EV06098, EV06110, EV06128, EV06136, EV06140, EV0644, EV06148, EV06154, EV06162, EV06166, EV06178, EV06188, EV07038 or combinations thereof.

3. The formulation of claim 1 or 2 wherein the nanoparticles (NP) have a size range of between about 100 nm and 500 nm.

4. A method for producing the formulation of claim 1 or 2 comprising the steps of:

(a) preparing a liquid phase comprising a solution of an active ingredient (AI) in a solvent or a mixture of solvents comprising one or more surfactant;

(b) preparing a second liquid phase comprising a non-solvent or the mixture of non-solvents for a substance that is miscible with the solvent or the mixture of solvents for the AI;

(c) adding one of the liquid phases prepared in (a) to (b) or (b) to (a) with stirring to produce a colloidal suspension of nanoparticles; and (d) optionally removing all or part of the solvent or the mixture of solvents to produce a colloidal suspension of nanoparticles of a desired concentration, thereby producing the formulation.

5. A method for producing a formulations having spherical nanoparticles of matrix type and size less than 500 nm, comprising the steps of:
   (a) preparing a liquid phase comprising a solution of AI+polymer in a solvent or a mixture of solvents to which one or more surfactants may be added;
   (b) preparing a second liquid phase comprising a non-solvent or a mixture of non-solvents to which one or more surfactant may be added, wherein the non-solvent or the mixture of non-solvents should be miscible in all proportions with the solvent or mixture of solvents of the AI;
   (c) adding the liquid phase prepared in (a) to that prepared in (b), or adding the liquid phase prepared in (b) to that prepared in (a), with moderate agitation to produce a colloidal suspension of nanoparticles;
   (d) optionally removing all or part of the solvent or the mixture of solvents and of non-solvent or mixture of non-solvent to make a colloidal nanoparticle suspension of a desired concentration.

6. The formulation of claim 1 or 2 that is in a form suitable for topical application to an animal.

7. The formulation of claim 1 or 2 that is a cream, gel, spray or spot-on.

8. A method of repelling pests comprising the step of applying the formulation of claim 1 or 2 to animals or a locus, thereby repelling pests.

9. The method of claim 8 wherein the animals are birds or mammals.

10. The method of claim 9 wherein the mammals are humans, equines, felines, canines, bovines, or caprines.

11. The method of 9 wherein the animals are equines or bovines.

12. The method of 9 wherein the animals are humans.

* * * * *